(12) United States Patent
Nath et al.

(10) Patent No.: US 7,396,823 B2
(45) Date of Patent: Jul. 8, 2008

(54) THERAPY INHALATION INVOLVING ANTISENSE OLIGONUCLEOTIDES FOR TREATING IDIOPATHIC PULMONARY FIBROSIS

(76) Inventors: Rahul K. Nath, 3754 Carlon St., Houston, TX (US) 77005; Rajinder Beri, 6 Braefell Close, West Brigford, Nottingham NG2 655 (GB)

( * ) Notice: Subject to any disclaimer, the term of this patent is extended or adjusted under 35 U.S.C. 154(b) by 152 days.

(21) Appl. No.: 11/021,603

(22) Filed: Dec. 21, 2004

(65) Prior Publication Data

US 2006/0003954 A1 Jan. 5, 2006

Related U.S. Application Data

(63) Continuation-in-part of application No. 10/149,352, filed as application No. PCT/GB00/04741 on Dec. 12, 2000, now Pat. No. 7,173,122.

(30) Foreign Application Priority Data

Dec. 15, 1999 (GB) .................................. 9929487.8

(51) Int. Cl.
*A61K 31/70* (2006.01)
(52) U.S. Cl. ....................................................... 514/44
(58) Field of Classification Search .................... None
See application file for complete search history.

*Primary Examiner*—Sean McGarry
*Assistant Examiner*—Louis Wollenberger
(74) *Attorney, Agent, or Firm*—The Matthews Firm

(57) ABSTRACT

The invention provides antisense DNA oligonucleotides which are effective in inhibiting the expression of a wild type COL1A1 gene, wherein said oligonucleotides are used in inhalation therapy to treat various lung diseases.

2 Claims, No Drawings

THERAPY INHALATION INVOLVING ANTISENSE OLIGONUCLEOTIDES FOR TREATING IDIOPATHIC PULMONARY FIBROSIS

RELATED APPLICATION

This application is a continuation-in-part of U.S. patent application Ser. No. 10/149,352, filed on Jun. 10, 2002 now U.S. Pat. No. 7,173,122, for Antisense Oligonucleotide, and claims priority from PCT/GB00/04741, filed Dec. 12, 2000, and from British Application No. 9929487.8, filed Dec. 15, 1999.

The sequence information required by MPEP 2422.05 is identical to the sequence information provided in U.S. patent application Ser. No. 10/149,352, filed on Jun. 10, 2002 identified above.

The present invention relates to antisense oligonucleotides and their use in inhibiting expression of type I procollagen.

The collagens are a family of closely related proteins, with a triple helix protein structure. Numerous collagen types have been identified (>10) of which type I procollagen (consisting of two alpha1 chains and one alpha2 chain) is the principal component of bone, skin, and tendon. It has been recognized for many years that many pathological conditions are caused by overproduction of collagen fibers in the form of scars and excess fibrous tissues. For example, liver cirrhosis is a two-step process in which normal liver tissue is first destroyed by a virus or by alcohol and other toxins, and then excessive amounts of collagen fibers replace the damaged cells before normal liver cell regeneration. Idiopathic pulmonary fibrosis ("IPF") is a lethal condition in which normal lung tissue is gradually replaced by excessive amounts of collagen fibers. Progressive systemic sclerosis (Scleroderma) is a frequently lethal disease where skin and many internal organs become leather-like because of excessive depositions of collagen fibers. In many individuals, wounds or surgical incisions in the skin are followed by excessive depositions of collagen in the form of hypertrophic scars and keloids that present cosmetic problems and sometimes more serious consequences. Also, excessive scarring frequently occurs in normal individuals following trauma and surgical procedures. In these and related conditions, a means of specifically inhibiting collagen synthesis and deposition would be tremendous benefit. PCT Patent Application Publication No. WO 94/11494 discloses a DNA or RNA oligonucleotide comprising from 5 to 200 nucleotides substantially complementary to a mutant collagen nucleotide sequence or normal wild type collagen nucleotide sequence which is capable of inhibiting collagen gene expression. Preferred oligonucleotides are said to be antisense oligonucleotides. The Examples of WO 94/11494 describe a series of DNA oligonucleotides, some of which are antisense, that were synthesized primarily with regard to the region at the 3' end of exon 1 (from nucleotides 198 to 222) and the first two nucleotides of intron 1 of the gene for the proα1 chains of type I procollagen (COL1A1). The synthesized oligonucleotides were found to vary considerably in their ability of inhibit expression of an internally deleted mutant COL1A1 gene of human origin. The effectiveness of the oligonucleotides in inhibiting the expression of the human wild type COL1A1 gene was not however demonstrated. Since the structure and conformation of the RNA, transcripts of the human, mutant and wild type COL1A1 genes would most likely differ, it would not necessarily follow that oligonucleotides which are effective inhibitors of the expression of the mutant COL1A1 gene would also be effective inhibitors of the expression of the wild type COL1A1 gene.

It would be desirable to identify antisense DNA oligonucleotides that are capable of inhibiting the expression of a wild type COL1A1 gene.

In accordance with the present invention, there is therefore provided an antisense DNA oligonucleotide comprising from 18 to 25 nucleotides which is complementary to a nucleotide sequence from position 750 to position 3000 inclusive of SEQ ID NO:1, wherein SEQ ID NO:1 comprises a nucleotide sequence encoding a polypeptide comprising an amino acid sequence according to SEQ ID No:2, the oligonucleotide being capable of inhibiting expression of the polypeptide in a cell that expresses it.

SEQ ID NO:1 is identical to the nucleotide sequence registered under EMBL accession no Z74615. SEQ ID NO:2 is the amino acid sequence of the polypeptide encoded by the nucleotide sequence of SEQ ID NO:1. The polypeptide encoded by SEQ ID NO:1 is a precursor of the wild type, proα1 chain of type I procollagen ("prepro-alpha1 (I) collagen").

The antisense DNA oligonucleotide according to the invention comprises 18, 19, 20, 21, 22, 23, 24 or 25 nucleotides and is preferably 20 nucleotides in length.

The antisense DNA oligonucleotide is preferably complementary to a nucleotide sequence in one of the following regions of SEQ ID NO:1,

| | |
|---|---|
| Region 1 | from position 750 to position 900 inclusive, |
| Region 2 | from position 1200 to position 1300 inclusive, |
| Region 3 | from position 1400 to position 1500 inclusive, |
| Region 4 | from position 1450 to position 1550 inclusive, |
| Region 5 | from position 1850 to position 2000 inclusive, |
| Region 6 | from position 2500 to position 2600 inclusive, |
| Region 7 | from position 2850 to position 2950 inclusive, |
| Region 8 | from position 2800 to position 3900 inclusive. |

Particularly preferred antisense DNA oligonucleotides are those which are complementary to a nucleotide sequence in Region 2, 4, 6 or 8 of SEQ ID NO:1

The oligonucleotides of the invention may be prepared by any suitable method known in the art. The oligonucleotides are very conveniently prepared by synthetic chemical methods, for example, phosphoramidite chemistry by sulfurization with tetraethylthiuram disulfide in acetonitrile as described in *Tetrahedron Lett.*, 1991, 32, 30005-30008.

The oligonucleotides of the present invention are advantageous in that they inhibit expression of the wild type COL1A1 gene. They are therefore useful in the treatment or prevention of conditions/disorders caused by overproduction of collagen fibers, for example, liver cirrhosis, kidney, liver and heart fibrosis, scleroderma, hypertrophic scars and keloids. Accordingly, the present invention provides an antisense DNA oligonucleotide according to the invention for the use in therapy.

In another aspect, the invention provides the use of an antisense DNA oligonucleotide according to the invention in the manufacture of a medicament for use in therapy.

In the context of the present specification, the term "therapy" also includes "prophylaxis" unless there are specific indications to the contrary. The terms "therapeutic" and "therapeutically" should be construed accordingly.

The invention further provides a method of treating, or reducing the risk of, a collagen disorder in a patient suffering from, or at risk of, the disorder, which comprises administering to the patient a therapeutically effective amount of an antisense DNA oligonucleotide according to the invention.

For the above-mentioned therapeutic uses the dosage administered will, of course, vary with the oligonucleotide employed, the mode of administration, the treatment desired and the disorder indicated. Effective dosages are those which are able to inhibit collagen protein production in cells at a level which eliminates or reduces the symptoms or conditions associated with the collagen protein production.

The oligonucleotides according to the invention will generally be administered in the form of a pharmaceutical composition in which the oligonucleotide is formulated with a pharmaceutically acceptable adjuvant, diluent or carrier.

Thus, the present invention also provides a pharmaceutical composition comprising an antisense DNA oligonucleotide according to the invention in association with a pharmaceutically acceptable adjuvant, diluent or carrier.

The invention further provides a process for the preparation of a pharmaceutical composition of the invention which comprises mixing the antisense DNA oligonucleotide with a pharmaceutically acceptable adjuvant, diluent or carrier.

The pharmaceutical compositor of the invention maybe administered topically in the form of, for example, a creme, lotion or ointment, or systemically, e.g. by oral administration in the form of tablets, capsules, syrups, powders or granules, or by parenteral administration in the form of sterile solutions or suspensions.

The invention also contemplates inhalation therapy for human patients having Idiopathic Pulmonary Fibrosis using a therapeutically effective dosage of the antisense DNA oligonucleotides, in a pharmaceutically acceptable adjuvant, diluent or carrier. Such adjuvants, diluents, and carriers are well known for use in inhalation therapy, and include various gases, vapors, powders, aerosols, and liquids. As but two examples, the antisense DNA oligonucleotides can be delivered to the patient's lungs through the use of various inhalers, which deliver the pharmaceutic composition according to the invention as an aerosol spray, and in addition, a nebulizer that delivers the pharmaceutical composition as a fine mist through a face mask.

In administering inhalation therapy according to the present invention to a patient having idiopathic pulmonary fibrosis, the therapeutically effective dosage will vary considerably based upon several factors. Since the disease is universally lethal, unless reversed, and based upon the underlying cause of the scarring and thickening of the lung tissue, and because the duration of the disease varies in the particular patient, as well as the age and general health of the patient, and the volume of the lung or lungs involved, the dosage will vary, along with the timing of repeat dosages, depending upon the response of the patient to the treatment.

Although by definition, a disease characterized as being idiopathic means that the cause of the disease is unknown, a biopsy of the fibrous lung tissue can sometimes determine the cause of the disease and the dosage for the inhalation therapy can be adjusted accordingly.

The present invention will now be further explained by reference to the following illustrative Examples.

EXAMPLES

Example 1

Oligonucleotide Synthesis

Phosphorothioate oligodeoxynucleotides synthesis was carried out in a 1 µm scale on PE Biosystems 394 DNA synthesizer using phosphoramidite chemistry with TETD/acetonitrile sulphurizing reagent. Oligonucleotides were purified on Poly-Pak TM II cartridges (Glen Research), desalted on NAP TM 10 columns (American Pharmacia Biotech AB) and ion-exchanged using Dowex 50WX8-100 ion exchange resin (Aldrich). Twelve antisense DNA oligonucleotides (ASOs) were prepared having the following sequences (5'→3'):

| 1.  | GGACGACCAGGTTTTCCAGC | (SEQ ID NO:3)  |
| --- | -------------------- | -------------- |
| 2.  | GCAGCACCAGCAGGGCCAGG | (SEQ ID NO:4)  |
| 3.  | GCCAGGAGCACCAGGTTCAC | (SEQ ID NO:5)  |
| 4.  | CTTCCTCTCCAGCAGGGCCA | (SEQ ID NO:6)  |
| 5.  | GCCTTGCCGGGCTCTCCAGC | (SEQ ID NO:7)  |
| 6.  | CGGGAACACCTCGCTCTCCA | (SEQ ID NO:8)  |
| 7.  | GCAGGACCGACAGCGCCAGG | (SEQ ID NO:9)  |
| 8.  | TCCATCTTTGCCAGCAGGAC | (SEQ ID NO:10) |
| 9.  | CGTCCCTGAGCTCCAGCCTC | (SEQ ID NO:11) |
| 10. | TTGGCCGTCAGCACCAGGG  | (SEQ ID NO:12) |
| 11. | TTTCTCGCCAGCAGGGCCAG | (SEQ ID NO:13) |
| 12. | CTCGATCTGCTGGCTCAGGC | (SEQ ID NO:14) |

Example 2

Treatment of Cells

The human cell line WI-26 was grown in Dulbecco's modified Eagle's medium (DMEM) containing 10% fetal calf serum. The cells were plated in 48-well plates (Costar, Corning Inc.) to obtain 70-80% confluence. After 24 hours, the cells were washed two times with pre-warmed DMEM and 0.35 ml (for 48-well experiments) or 1 ml (6-well experiments) DMEM containing 5 µg/ml lipofection (Gibco BRL) or 2.5 µg/ml cytofectin GSV (Glen Research Ltd) and oligonucleotides at 200 nM were added to each well. After 4-5 hours at 37° C. the cells were washed two times with pre-warmed DMEM and 0.35 ml DMEM (48-well plates) or 1 ml DMEM (6 well plates) was added together with ascorbic acid at 10 µg/ml. The cells were incubated for 20 hours prior to analysis of collagen levels.

Example 3

Protein Analysis

At the end of the experiment, 150 µl of medium was removed and the amount of secreted type I procollagen determined using an ELISA kit (AmershamPharmacia Ltd) and the results expressed as nanograms of procollagen in the medium/10,000 cells. To correct for cell numbers, plates were washed with pre-warmed PBS, cells treated with trypsin and cell numbers determined using a automated Coulter counter. For 6-well experiments, the cells were counted, treated with 1 ml TRI reagent (SIGMA Ltd) and proteins and RNA extracted according to the manufacturers guidelines. The protein pellet was re-suspended in 1% SDS containing protease inhibitors. 30-100 µgs cellular proteins were heated at 100° C. for 5 minutes and then lectrophoresed in a 4-12% SDS polyacrylamide gel. Proteins were electrophoretically transferred to nitrocellulose filters and hybridized with an antibody against a synthetic peptide corresponding to human proα(I)

chain of type 1 collagen (obtained from Dr. Larry Fisher, NIH, USA). The proα1(1) band was detected using ECL (Pierce Ltd). Protein loading was determined by treating the membrane with an antibody to GAPDH (Advanced Immunochemicals). Protein loading was normalized to GAPDH levels using desitometry.

Example 4

RNA Analysis

RNA was extracted using TRI reagent and the final pellet was re-suspended in 0.5% SDS. One to three micrograms of total RNA were electrophoresed in a formaldehyde denaturing gel according to standard procedures (Sambrook, J., Fritsch, E. F. and Maniatis, T. (1989) Molecular Cloning: A Laboratory Manual, $2^{nd}$ Ed., Cold Spring Harbor Laboratory Press, (Amersham) and hybridized for 24 hours to an alpha1 (1) cDNA probe radiolabeled using a T7 polymerase kit (AmershamPharmacia). Following washing, the filter was exposed to X-ray film and the film developed 4-24 hours later. The autoradiographic images of the alpha1(1) transcripts (4.8 kb & 5.8 kb) were analyzed by densitometric analysis and RNA loading was corrected using the intensity of the GAPDH transcript or the intensity of the 28S rRNA as internal controls.

Results

Table I below shows the average percentage (%) collagen inhibition which related to either collagen levels in the medium or collagen mRNA levels. In the treated cell assay used, there was a very good correlation between percentage collagen inhibitation as measured in the medium and percentage inhibition of intracellular collagen mRNA levels.

TABLE I

| ASO | | AVERAGE % COLLAGEN INHIBITION |
|---|---|---|
| CGACGACCAGGTTTTCCAGC | (SEQ ID NO:3) | 50 |
| GCAGCACCAGCACCAGGTTCAC | (SEQ ID NO:4) | 50-80 |
| GCCAGGAGCACCAGGTTCAC | (SEQ ID NO:5) | 50 |
| CTTCCTCTCCAGCAGGGCCA | (SEQ ID NO:6) | 50-60 |
| GCCTTGCGGGCTCC TCCAGC | (SEQ ID NO:7) | 50 |
| CGGGAACACCTCGCTCTCCA | (SEQ ID NO:8) | 50 |
| GCAGGACCGACAGCGCCAGG | (SEQ ID NO:9) | 50 |
| TCCATCTTTGCCAGCAGGAC | (SEQ ID NO:10) | 50 |
| GGTCCCTGAGCTCCAGCCTC | (SEQ ID NO:11) | 50 |
| TTGGCCGTCAGCACCAGGG | (SEQ ID NO:12) | 50-80 |
| TTTCTCGCCAGCAGGGCCAG | (SEQ ID NO:13) | 50-70 |
| CTCGATCTGCTGGCTCAGGC | (SEQ ID NO:14) | 50-80 |

The invention claimed is:

1. A method of treating a collagen disorder in a patient suffering from, a lung disease relating to the collagen disorder, which comprises administering inhalation therapy to the patient using a therapeutically effective amount of an antisense DNA oligonucleotide having SEQ ID NO:14.

2. The method according to claim 1, wherein said oligonucleotide is administered in association with a pharmaceutically acceptable adjuvant, diluent, or carrier.

* * * * *

SEQUENCE LISTING

```
<160> NUMBER OF SEQ ID NOS: 14

<210> SEQ ID NO 1
<211> LENGTH: 6728
<212> TYPE: DNA
<213> ORGANISM: Homo sapiens
<220> FEATURE:
<221> NAME/KEY: CDS
<222> LOCATION: (120)..(4511)
<220> FEATURE:
<221> NAME/KEY: sig_peptide
<222> LOCATION: (120)..(185)

<400> SEQUENCE: 1
agcagacggg agtttctcct cggggtcgga gcaggaggca cgcggagtgt gaggccacgc      60
atgagcggac gctaaccccc tccccagcca caaagagtct acatgtctag ggtctagac     119 atg ttc agc ttt gtg gac ctc cgg ctc ctg ctc ctc tta gcg gcc acc      167
Met Phe Ser Phe Val Asp Leu Arg Leu Leu Leu Leu Leu Ala Ala Thr
  1               5                  10                  15 gcc ctg ctg acg cac ggc caa gag gaa ggc caa gtc gag ggc caa gac      215
Ala Leu Leu Thr His Gly Gln Glu Glu Gly Gln Val Glu Gly Gln Asp
             20                  25                  30 gaa gac atc cca cca atc acc tgc gta cag aac ggc ctc agg tac cat      263
Glu Asp Ile Pro Pro Ile Thr Cys Val Gln Asn Gly Leu Arg Tyr His
         35                  40                  45 gac cga gac gtg tgg aaa ccc gag ccc tgc cgg atc tgc gtc tgc gac      311
Asp Arg Asp Val Trp Lys Pro Glu Pro Cys Arg Ile Cys Val Cys Asp
     50                  55                  60 aac ggc aag gtg ttg tgc gat gac gtg atc tgt gac gag acc aag aac      359
Asn Gly Lys Val Leu Cys Asp Asp Val Ile Cys Asp Glu Thr Lys Asn
```

-continued

```
            65                  70                  75                  80
tgc ccc ggc gcc gaa gtc ccc gag ggc gag tgc tgt ccc gtc tgc ccc        407
Cys Pro Gly Ala Glu Val Pro Glu Gly Glu Cys Cys Pro Val Cys Pro
                    85                  90                  95 gac ggc tca gag tca ccc acc gac caa gaa acc acc ggc gtc gag gga        455
Asp Gly Ser Glu Ser Pro Thr Asp Gln Glu Thr Thr Gly Val Glu Gly
                100                 105                 110 ccc aag gga gac act ggc ccc cga ggc cca agg gga ccc gca ggc ccc        503
Pro Lys Gly Asp Thr Gly Pro Arg Gly Pro Arg Gly Pro Ala Gly Pro
            115                 120                 125 cct ggc cga gat ggc atc cct gga cag cct gga ctt ccc gga ccc ccc        551
Pro Gly Arg Asp Gly Ile Pro Gly Gln Pro Gly Leu Pro Gly Pro Pro
        130                 135                 140 gga ccc ccc gga cct ccc gga ccc cct ggc ctc gga gga aac ttt gct        599
Gly Pro Pro Gly Pro Pro Gly Pro Pro Gly Leu Gly Gly Asn Phe Ala
    145                 150                 155                 160 ccc cag ctg tct tat ggc tat gat gag aaa tca acc gga gga att tcc        647
Pro Gln Leu Ser Tyr Gly Tyr Asp Glu Lys Ser Thr Gly Gly Ile Ser
                165                 170                 175 gtg cct ggc ccc atg ggt ccc tct ggt cct cgt ggt ctc cct ggc ccc        695
Val Pro Gly Pro Met Gly Pro Ser Gly Pro Arg Gly Leu Pro Gly Pro
                180                 185                 190 cct ggt gca cct ggt ccc caa ggc ttc caa ggt ccc cct ggt gag cct        743
Pro Gly Ala Pro Gly Pro Gln Gly Phe Gln Gly Pro Pro Gly Glu Pro
            195                 200                 205 ggc gag cct gga gct tca ggt ccc atg ggt ccc cga ggt ccc cca ggt        791
Gly Glu Pro Gly Ala Ser Gly Pro Met Gly Pro Arg Gly Pro Pro Gly
        210                 215                 220 ccc cct gga aag aat gga gat gat ggg gaa gct gga aaa cct ggt cgt        839
Pro Pro Gly Lys Asn Gly Asp Asp Gly Glu Ala Gly Lys Pro Gly Arg
225                 230                 235                 240 cct ggt gag cgt ggg cct cct ggg cct cag ggt gct cga gga ttg ccc        887
Pro Gly Glu Arg Gly Pro Pro Gly Pro Gln Gly Ala Arg Gly Leu Pro
                245                 250                 255 gga aca gct ggc ctc cct gga atg aag gga cac aga ggt ttc agt ggt        935
Gly Thr Ala Gly Leu Pro Gly Met Lys Gly His Arg Gly Phe Ser Gly
            260                 265                 270 ttg gat ggt gcc aag gga gat gct ggt cct gct ggt cct aag ggt gag        983
Leu Asp Gly Ala Lys Gly Asp Ala Gly Pro Ala Gly Pro Lys Gly Glu
        275                 280                 285 cct ggc agc cct ggt gaa aat gga gct cct ggt cag atg ggc ccc cgt       1031
Pro Gly Ser Pro Gly Glu Asn Gly Ala Pro Gly Gln Met Gly Pro Arg
    290                 295                 300 ggc ctg cct ggt gag aga ggt cgc cct gga gcc cct ggc cct gct ggt       1079
Gly Leu Pro Gly Glu Arg Gly Arg Pro Gly Ala Pro Gly Pro Ala Gly
305                 310                 315                 320 gct cgt gga aat gat ggt gct act ggt gct gcc ggg ccc cct ggt ccc       1127
Ala Arg Gly Asn Asp Gly Ala Thr Gly Ala Ala Gly Pro Pro Gly Pro
                325                 330                 335 acc ggc ccc gct ggt cct cct ggc ttc cct ggt gct gtt ggt gct aag       1175
Thr Gly Pro Ala Gly Pro Pro Gly Phe Pro Gly Ala Val Gly Ala Lys
            340                 345                 350 ggt gaa gct ggt ccc caa ggg ccc cga ggc tct gaa ggt ccc cag ggt       1223
Gly Glu Ala Gly Pro Gln Gly Pro Arg Gly Ser Glu Gly Pro Gln Gly
        355                 360                 365 gtg cgt ggt gag cct ggc ccc cct ggc cct gct ggt gct gct ggc cct       1271
Val Arg Gly Glu Pro Gly Pro Pro Gly Pro Ala Gly Ala Ala Gly Pro
    370                 375                 380 gct gga aac cct ggt gct gat gga cag cct ggt gct aaa ggt gcc aat       1319
```

-continued

```
                Ala Gly Asn Pro Gly Ala Asp Gly Gln Pro Gly Ala Lys Gly Ala Asn
                385                 390                 395                 400 ggt gct cct ggt att gct ggt gct cct ggc ttc cct ggt gcc cga ggc        1367
Gly Ala Pro Gly Ile Ala Gly Ala Pro Gly Phe Pro Gly Ala Arg Gly
                405                 410                 415 ccc tct gga ccc cag ggc ccc ggc ggc cct cct ggt ccc aag ggt aac        1415
Pro Ser Gly Pro Gln Gly Pro Gly Gly Pro Pro Gly Pro Lys Gly Asn
                420                 425                 430 agc ggt gaa cct ggt gct cct ggc agc aaa gga gac act ggt gct aag        1463
Ser Gly Glu Pro Gly Ala Pro Gly Ser Lys Gly Asp Thr Gly Ala Lys
                435                 440                 445 gga gag cct ggc cct gtt ggt gtt caa gga ccc cct ggc cct gct gga        1511
Gly Glu Pro Gly Pro Val Gly Val Gln Gly Pro Pro Gly Pro Ala Gly
450                 455                 460 gag gaa gga aag cga gga gct cga ggt gaa ccc gga ccc act ggc ctg        1559
Glu Glu Gly Lys Arg Gly Ala Arg Gly Glu Pro Gly Pro Thr Gly Leu
465                 470                 475                 480 ccc gga ccc cct ggc gag cgt ggt gga cct ggt agc cgt ggt ttc cct        1607
Pro Gly Pro Pro Gly Glu Arg Gly Gly Pro Gly Ser Arg Gly Phe Pro
                485                 490                 495 ggc gca gat ggt gtt gct ggt ccc aag ggt ccc gct ggt gaa cgt ggt        1655
Gly Ala Asp Gly Val Ala Gly Pro Lys Gly Pro Ala Gly Glu Arg Gly
                500                 505                 510 tct cct ggc ccc gct ggc ccc aaa gga tct cct ggt gaa gct ggt cgt        1703
Ser Pro Gly Pro Ala Gly Pro Lys Gly Ser Pro Gly Glu Ala Gly Arg
                515                 520                 525 ccc ggt gaa gct ggt ctg cct ggt gcc aag ggt ctg act gga agc cct        1751
Pro Gly Glu Ala Gly Leu Pro Gly Ala Lys Gly Leu Thr Gly Ser Pro
530                 535                 540 ggc agc cct ggt cct gat ggc aaa act ggc ccc cct ggt ccc gcc ggt        1799
Gly Ser Pro Gly Pro Asp Gly Lys Thr Gly Pro Pro Gly Pro Ala Gly
545                 550                 555                 560 caa gat ggt cgc ccc gga ccc cca ggc cca cct ggt gcc cgt ggt cag        1847
Gln Asp Gly Arg Pro Gly Pro Pro Gly Pro Pro Gly Ala Arg Gly Gln
                565                 570                 575 gct ggt gtg atg gga ttc cct gga cct aaa ggt gct gct gga gag ccc        1895
Ala Gly Val Met Gly Phe Pro Gly Pro Lys Gly Ala Ala Gly Glu Pro
                580                 585                 590 ggc aag gct gga gag cga ggt gtt ccc gga ccc cct ggc gct gtc ggt        1943
Gly Lys Ala Gly Glu Arg Gly Val Pro Gly Pro Pro Gly Ala Val Gly
                595                 600                 605 cct gct ggc aaa gat gga gag gct gga gct cag gga ccc cct ggc cct        1991
Pro Ala Gly Lys Asp Gly Glu Ala Gly Ala Gln Gly Pro Pro Gly Pro
610                 615                 620 ggt ggt ccc gct ggc gag aga ggt gaa caa ggc cct gct ggc tcc ccc        2039
Ala Gly Pro Ala Gly Glu Arg Gly Glu Gln Gly Pro Ala Gly Ser Pro
625                 630                 635                 640 gga ttc cag ggt ctc cct ggt cct gct ggt cct cca ggt gaa gca ggc        2087
Gly Phe Gln Gly Leu Pro Gly Pro Ala Gly Pro Pro Gly Glu Ala Gly
                645                 650                 655 aaa cct ggt gaa cag ggt gtt cct gga gac ctt ggc gcc cct ggc ccc        2135
Lys Pro Gly Glu Gln Gly Val Pro Gly Asp Leu Gly Ala Pro Gly Pro
                660                 665                 670 tct gga gca aga ggc gag aga ggt ttc cct ggc gag cgt ggt gtg caa        2183
Ser Gly Ala Arg Gly Glu Arg Gly Phe Pro Gly Glu Arg Gly Val Gln
                675                 680                 685 ggt ccc cct ggt cct gct gga ccc cga ggg gcc aac ggt gct ccc ggc        2231
Gly Pro Pro Gly Pro Ala Gly Pro Arg Gly Ala Asn Gly Ala Pro Gly
690                 695                 700
```

```
                                                        -continued aac gat ggt gct aag ggt gat gct gga gcc cct gga gct ccc ggt agc         2279
Asn Asp Gly Ala Lys Gly Asp Ala Gly Ala Pro Gly Ala Pro Gly Ser
705                 710                 715                 720 cag ggc gcc cct ggc ctt cag gga atg cct ggt gaa cgt ggt gca gct         2327
Gln Gly Ala Pro Gly Leu Gln Gly Met Pro Gly Glu Arg Gly Ala Ala
                725                 730                 735 ggt ctt cca ggg cct aag ggt gac aga ggt gat gct ggt ccc aaa ggt         2375
Gly Leu Pro Gly Pro Lys Gly Asp Arg Gly Asp Ala Gly Pro Lys Gly
            740                 745                 750 gct gat ggc tct cct ggc aaa gat ggc gtc cgt ggt ctg acc ggc ccc         2423
Ala Asp Gly Ser Pro Gly Lys Asp Gly Val Arg Gly Leu Thr Gly Pro
        755                 760                 765 att ggt cct cct ggc cct gct ggt gcc cct ggt gac aag ggt gaa agt         2471
Ile Gly Pro Pro Gly Pro Ala Gly Ala Pro Gly Asp Lys Gly Glu Ser
770                 775                 780 ggt ccc agc ggc cct gct ggt ccc act gga gct cgt ggt gcc ccc gga         2519
Gly Pro Ser Gly Pro Ala Gly Pro Thr Gly Ala Arg Gly Ala Pro Gly
785                 790                 795                 800 gac cgt ggt gag cct ggt ccc ccc ggc cct gct ggc ttt gct ggc ccc         2567
Asp Arg Gly Glu Pro Gly Pro Pro Gly Pro Ala Gly Phe Ala Gly Pro
                805                 810                 815 cct ggt gct gac ggc caa cct ggt gct aaa ggc gaa cct ggt gat gct         2615
Pro Gly Ala Asp Gly Gln Pro Gly Ala Lys Gly Glu Pro Gly Asp Ala
            820                 825                 830 ggt gcc aaa ggc gat gct ggt ccc cct ggg cct gcc gga ccc gct gga         2663
Gly Ala Lys Gly Asp Ala Gly Pro Pro Gly Pro Ala Gly Pro Ala Gly
        835                 840                 845 ccc cct ggc ccc att ggt aat gtt ggt gct cct gga gcc aaa ggt gct         2711
Pro Pro Gly Pro Ile Gly Asn Val Gly Ala Pro Gly Ala Lys Gly Ala
850                 855                 860 cgc ggc agc gct ggt ccc cct ggt gct act ggt ttc cct ggt gct gct         2759
Arg Gly Ser Ala Gly Pro Pro Gly Ala Thr Gly Phe Pro Gly Ala Ala
865                 870                 875                 880 ggc cga gtc ggt cct cct ggc ccc tct gga aat gct gga ccc cct ggc         2807
Gly Arg Val Gly Pro Pro Gly Pro Ser Gly Asn Ala Gly Pro Pro Gly
                885                 890                 895 cct cct ggt cct gct ggc aaa gaa ggc ggc aaa ggt ccc cgt ggt gag         2855
Pro Pro Gly Pro Ala Gly Lys Glu Gly Gly Lys Gly Pro Arg Gly Glu
            900                 905                 910 act ggc cct gct gga cgt cct ggt gaa gtt ggc ccc cct ggt ccc cct         2903
Thr Gly Pro Ala Gly Arg Pro Gly Glu Val Gly Pro Pro Gly Pro Pro
        915                 920                 925 ggc cct gct ggc gag aaa gga tcc cct ggt gct gat ggt cct gct ggt         2951
Gly Pro Ala Gly Glu Lys Gly Ser Pro Gly Ala Asp Gly Pro Ala Gly
930                 935                 940 gct cct ggt act ccc ggg cct caa ggt att gct gga cag cgt ggt gtg         2999
Ala Pro Gly Thr Pro Gly Pro Gln Gly Ile Ala Gly Gln Arg Gly Val
945                 950                 955                 960 gtc ggc ctg cct ggt cag aga gga gag aga ggc ttc cct ggt ctt cct         3047
Val Gly Leu Pro Gly Gln Arg Gly Glu Arg Gly Phe Pro Gly Leu Pro
                965                 970                 975 ggc ccc tct ggt gaa cct ggc aaa caa ggt ccc tct gga gca agt ggt         3095
Gly Pro Ser Gly Glu Pro Gly Lys Gln Gly Pro Ser Gly Ala Ser Gly
            980                 985                 990 gaa cgt ggt ccc ccc ggt ccc atg ggc ccc cct gga ttg gct gga ccc         3143
Glu Arg Gly Pro Pro Gly Pro Met Gly Pro Pro Gly Leu Ala Gly Pro
        995                 1000                1005 cct ggt gaa tct gga cgt gag ggg gct cct gct gcc gaa ggt tcc cct         3191
Pro Gly Glu Ser Gly Arg Glu Gly Ala Pro Ala Ala Glu Gly Ser Pro
    1010                1015                1020
```

-continued

| | |
|---|---|
| gga cga gac ggt tct cct ggc gcc aag ggt gac cgt ggt gag acc ggc<br>Gly Arg Asp Gly Ser Pro Gly Ala Lys Gly Asp Arg Gly Glu Thr Gly<br>1025                     1030                     1035                     1040 | 3239 |
| ccc gct gga ccc cct ggt gct cct ggt gct cct ggt gcc cct ggc ccc<br>Pro Ala Gly Pro Pro Gly Ala Pro Gly Ala Pro Gly Ala Pro Gly Pro<br>             1045                     1050                     1055 | 3287 |
| gtt ggc cct gct ggc aag agt ggt gat cgt ggt gag act ggt cct gct<br>Val Gly Pro Ala Gly Lys Ser Gly Asp Arg Gly Glu Thr Gly Pro Ala<br>1060                     1065                     1070 | 3335 |
| ggt ccc gcc ggt ccc gtc ggc ccc gtc ggc gcc cgt ggc ccc gcc gga<br>Gly Pro Ala Gly Pro Val Gly Pro Val Gly Ala Arg Gly Pro Ala Gly<br>             1075                     1080                     1085 | 3383 |
| ccc caa ggc ccc cgt ggt gac aag ggt gag aca ggc gaa cag ggc gac<br>Pro Gln Gly Pro Arg Gly Asp Lys Gly Glu Thr Gly Glu Gln Gly Asp<br>      1090                     1095                     1100 | 3431 |
| aga ggc ata aag ggt cac cgt ggc ttc tct ggc ctc cag ggt ccc cct<br>Arg Gly Ile Lys Gly His Arg Gly Phe Ser Gly Leu Gln Gly Pro Pro<br>1105                     1110                     1115                     1120 | 3479 |
| ggc cct cct ggc tct cct ggt gaa caa ggt ccc tct gga gcc tct ggt<br>Gly Pro Pro Gly Ser Pro Gly Glu Gln Gly Pro Ser Gly Ala Ser Gly<br>             1125                     1130                     1135 | 3527 |
| cct gct ggt ccc cga ggt ccc cct ggc tct gct ggt gct cct ggc aaa<br>Pro Ala Gly Pro Arg Gly Pro Pro Gly Ser Ala Gly Ala Pro Gly Lys<br>             1140                     1145                     1150 | 3575 |
| gat gga ctc aac ggt ctc cct ggc ccc att ggg ccc cct ggt cct cgc<br>Asp Gly Leu Asn Gly Leu Pro Gly Pro Ile Gly Pro Pro Gly Pro Arg<br>             1155                     1160                     1165 | 3623 |
| ggt cgc act ggt gat gct ggt cct gtt ggt ccc ccc ggc cct cct gga<br>Gly Arg Thr Gly Asp Ala Gly Pro Val Gly Pro Pro Gly Pro Pro Gly<br>1170                     1175                     1180 | 3671 |
| cct cct ggt ccc cct ggt cct ccc agc gct ggt ttc gac ttc agc ttc<br>Pro Pro Gly Pro Pro Gly Pro Pro Ser Ala Gly Phe Asp Phe Ser Phe<br>1185                     1190                     1195                     1200 | 3719 |
| ctg ccc cag cca cct caa gag aag gct cac gat ggt ggc cgc tac tac<br>Leu Pro Gln Pro Pro Gln Glu Lys Ala His Asp Gly Gly Arg Tyr Tyr<br>             1205                     1210                     1215 | 3767 |
| cgg gct gat gat gcc aat gtg gtt cgt gac cgt gac ctc gag gtg gac<br>Arg Ala Asp Asp Ala Asn Val Val Arg Asp Arg Asp Leu Glu Val Asp<br>             1220                     1225                     1230 | 3815 |
| acc acc ctc aag agc ctg agc cag cag atc gag aac atc cgg agc cca<br>Thr Thr Leu Lys Ser Leu Ser Gln Gln Ile Glu Asn Ile Arg Ser Pro<br>1235                     1240                     1245 | 3863 |
| gag gga agc cgc aag aac ccc gcc cgc acc tgc cgt gac ctc aag atg<br>Glu Gly Ser Arg Lys Asn Pro Ala Arg Thr Cys Arg Asp Leu Lys Met<br>    1250                     1255                     1260 | 3911 |
| tgc cac tct gac tgg aag agt gga gag tac tgg att gac ccc aac caa<br>Cys His Ser Asp Trp Lys Ser Gly Glu Tyr Trp Ile Asp Pro Asn Gln<br>1265                     1270                     1275                     1280 | 3959 |
| ggc tgc aac ctg gat gcc atc aaa gtc ttc tgc aac atg gag act ggt<br>Gly Cys Asn Leu Asp Ala Ile Lys Val Phe Cys Asn Met Glu Thr Gly<br>             1285                     1290                     1295 | 4007 |
| gag acc tgc gtg tac ccc act cag ccc agt gtg gcc cag aag aac tgg<br>Glu Thr Cys Val Tyr Pro Thr Gln Pro Ser Val Ala Gln Lys Asn Trp<br>             1300                     1305                     1310 | 4055 |
| tac atc agc aag aac ccc aag gac aag agg cat gtc tgg ttc ggc gag<br>Tyr Ile Ser Lys Asn Pro Lys Asp Lys Arg His Val Trp Phe Gly Glu<br>             1315                     1320                     1325 | 4103 |
| agc atg acc gat gga ttc cag ttc gag tat ggc ggc cag ggc tcc gac<br>Ser Met Thr Asp Gly Phe Gln Phe Glu Tyr Gly Gly Gln Gly Ser Asp | 4151 |

-continued

```
              1330              1335              1340
cct gcc gat gtg gcc atc cag ctg acc ttc ctg cgc ctg atg tcc acc         4199
Pro Ala Asp Val Ala Ile Gln Leu Thr Phe Leu Arg Leu Met Ser Thr
1345              1350              1355              1360 gag gcc tcc cag aac atc acc tac cac tgc aag aac agc gtg gcc tac         4247
Glu Ala Ser Gln Asn Ile Thr Tyr His Cys Lys Asn Ser Val Ala Tyr
              1365              1370              1375 atg gac cag cag act ggc aac ctc aag aag gcc ctg ctc ctc aag ggc         4295
Met Asp Gln Gln Thr Gly Asn Leu Lys Lys Ala Leu Leu Leu Lys Gly
         1380              1385              1390 tcc aac gag atc gag atc cgc gcc gag ggc aac agc cgc ttc acc tac         4343
Ser Asn Glu Ile Glu Ile Arg Ala Glu Gly Asn Ser Arg Phe Thr Tyr
    1395              1400              1405 agc gtc act gtc gat ggc tgc acg agt cac acc gga gcc tgg ggc aag         4391
Ser Val Thr Val Asp Gly Cys Thr Ser His Thr Gly Ala Trp Gly Lys
    1410              1415              1420 aca gtg att gaa tac aaa acc acc aag tcc tcc cgc ctg ccc atc atc         4439
Thr Val Ile Glu Tyr Lys Thr Thr Lys Ser Ser Arg Leu Pro Ile Ile
1425              1430              1435              1440 gat gtg gcc ccc ttg gac gtt ggt gcc cca gac cag gaa ttc ggc ttc         4487
Asp Val Ala Pro Leu Asp Val Gly Ala Pro Asp Gln Glu Phe Gly Phe
              1445              1450              1455 gac gtt ggc cct gtc tgc ttc ctg taaactcccc catcccaac ctggctccct         4541
Asp Val Gly Pro Val Cys Phe Leu
              1460 cccacccaac caactttccc ccaacccgg aaacagacaa gcaacccaaa ctgaacccc        4601
ccaaaagcca aaaatggga cacaatttca catggacttt ggaaaatatt ttttcctttt     4661
gcattcatct ctcaaactta gtttttatct ttgaccaacc gaacatgacc aaaaaccaaa     4721
agtgcattca accttaccaa aaaaaaaaaa aaaaaaaaa gaataaataa ataagttttt     4781
aaaaaaggaa gcttggtcca cttgcttgaa gacccatgcg ggggtaagtc cctttctgcc    4841
cgttgggtta tgaaacccca atgctgccct ttctgctcct ttctccacac ccccttggc      4901
ctcccctcca ctccttccca aatctgtctc cccagaagac acaggaaaca atgtattgtc    4961
tgcccagcaa tcaaaggcaa tgctcaaaca cccaagtggc ccccaccctc agcccgctcc    5021
tgcccgccca gcaccccag gccctgggga cctggggttc tcagactgcc aaagaagcct    5081
tgccatctgg cgctcccatg gctcttgcaa catctcccct tcgttttttga gggggtcatg   5141
ccggggagc caccagcccc tcactgggtt cggaggagag tcaggaaggg ccacgacaaa    5201
gcagaaacat cggatttggg aacgcgtgt catcccttgt gccgcaggct gggcgggaga    5261
gactgttctg ttctgttcct tgtgtaactg tgttgctgaa agactacctc gttcttgtct    5321
tgatgtgtca ccggggcaac tgcctggggg cggggatggg ggcagggtgg aagcggctcc    5381
ccatttttat accaaaggtg ctacatctat gtgatgggtg gggtggggag ggaatcactg    5441
gtgctataga aattgagatg ccccccccagg ccagcaaatg ttccttttttg ttcaaagtct   5501
attttttattc cttgatattt tttctttctt tttttttttt tttgtggatg gggacttgtg    5561
aattttctta aaggtgctat ttaacatggg aggagagcgt gtgcgctcca gcccagcccg    5621
ctgctcactt tccaccctct ctccacctgc ctctggcttc tcaggcctct gctctccgac    5681
ctctctcctc tgaaaccctc ctccacagct gcagcccatc ctcccggctc cctcctagtc    5741
tgtcctgcgt cctctgtccc cgggtttcag agacaacttc ccaaagcaca aagcagtttt    5801
tccctagggg tgggaggaag caaaagactc tgtacctatt ttgtatgtgt ataataattt    5861
gagatgtttt taattatttt gattgctgga ataaagcatg tggaaatgac ccaaacataa    5921
```

```
                                                             -continued tccgcagtgg cctcctaatt tccttctttg gagttggggg aggggtagac atggggaagg     5981
ggccttgggg tgatgggctt gccttccatt cctgccctttt ccctccccac tattctcttc    6041
tagatccctc cataacccca ctccccttc tctcaccctt cttataccgc aaacctttct     6101
acttcctctt tcattttcta ttccttgcaat ttccttgcac cttttccaaa tcctcttctc    6161
ccctgcaata ccatacaggc aatccacgtg cacaacacac acacacactc ttcacatctg    6221
gggttgtcca aacctcatac ccactcccct tcaagcccat ccactctcca cccctggat     6281 gccctgcact tggtggcggt gggatgctca tggatactgg gagggtgagg ggagtggaac    6341
ccgtgaggag gacctggggg cctctccttg aactgacatg aagggtcatc tggcctctgc    6401
tcccttctca cccacgctga cctcctgccg aaggagcaac gcaacaggag aggggtctgc    6461
tgagcctggc gagggtctgg gagggaccag gaggaaggcg tgctccctgc tcgctgtcct    6521
ggccctgggg gagtgaggga gacagacacc tgggagagct gtggggaagg cactcgcacc    6581
gtgctcttgg gaaggaagga gacctggccc tgctcaccac ggactgggtg cctcgacctc    6641
ctgaatcccc agaacacaac cccctgggc tggggtggtc tggggaacca tcgtgccccc     6701
gcctcccgcc tactccttttt taagctt                                        6728

<210> SEQ ID NO 2
<211> LENGTH: 1464
<212> TYPE: PRT
<213> ORGANISM: Homo sapiens

<400> SEQUENCE: 2

Met Phe Ser Phe Val Asp Leu Arg Leu Leu Leu Leu Ala Ala Thr
  1               5                  10                  15

Ala Leu Leu Thr His Gly Gln Glu Glu Gly Gln Val Glu Gly Gln Asp
                 20                  25                  30

Glu Asp Ile Pro Pro Ile Thr Cys Val Gln Asn Gly Leu Arg Tyr His
             35                  40                  45

Asp Arg Asp Val Trp Lys Pro Glu Pro Cys Arg Ile Cys Val Cys Asp
         50                  55                  60

Asn Gly Lys Val Leu Cys Asp Asp Val Ile Cys Asp Glu Thr Lys Asn
 65                  70                  75                  80

Cys Pro Gly Ala Glu Val Pro Glu Gly Glu Cys Cys Pro Val Cys Pro
                 85                  90                  95

Asp Gly Ser Glu Ser Pro Thr Asp Gln Glu Thr Thr Gly Val Glu Gly
            100                 105                 110

Pro Lys Gly Asp Thr Gly Pro Arg Gly Pro Arg Gly Pro Ala Gly Pro
            115                 120                 125

Pro Gly Arg Asp Gly Ile Pro Gly Gln Pro Gly Leu Pro Gly Pro Pro
        130                 135                 140

Gly Pro Pro Gly Pro Pro Gly Pro Pro Gly Leu Gly Gly Asn Phe Ala
145                 150                 155                 160

Pro Gln Leu Ser Tyr Gly Tyr Asp Glu Lys Ser Thr Gly Gly Ile Ser
                165                 170                 175

Val Pro Gly Pro Met Gly Pro Ser Gly Pro Arg Gly Leu Pro Gly Pro
            180                 185                 190

Pro Gly Ala Pro Gly Pro Gln Gly Phe Gln Gly Pro Pro Gly Glu Pro
            195                 200                 205

Gly Glu Pro Gly Ala Ser Gly Pro Met Gly Pro Arg Gly Pro Pro Gly
        210                 215                 220
```

-continued

```
Pro Pro Gly Lys Asn Gly Asp Gly Glu Ala Gly Lys Pro Gly Arg
225                 230                 235                 240

Pro Gly Glu Arg Gly Pro Gly Pro Gln Gly Ala Arg Gly Leu Pro
            245                 250                 255

Gly Thr Ala Gly Leu Pro Gly Met Lys Gly His Arg Gly Phe Ser Gly
                260                 265                 270

Leu Asp Gly Ala Lys Gly Asp Ala Gly Pro Ala Gly Pro Lys Gly Glu
            275                 280                 285

Pro Gly Ser Pro Gly Glu Asn Gly Ala Pro Gly Gln Met Gly Pro Arg
        290                 295                 300

Gly Leu Pro Gly Glu Arg Gly Arg Pro Gly Ala Pro Gly Pro Ala Gly
305                 310                 315                 320

Ala Arg Gly Asn Asp Gly Ala Thr Gly Ala Ala Gly Pro Pro Gly Pro
                325                 330                 335

Thr Gly Pro Ala Gly Pro Pro Gly Phe Pro Gly Ala Val Gly Ala Lys
            340                 345                 350

Gly Glu Ala Gly Pro Gln Gly Pro Arg Gly Ser Glu Gly Pro Gln Gly
            355                 360                 365

Val Arg Gly Glu Pro Gly Pro Pro Gly Pro Ala Gly Ala Ala Gly Pro
370                 375                 380

Ala Gly Asn Pro Gly Ala Asp Gly Gln Pro Gly Ala Lys Gly Ala Asn
385                 390                 395                 400

Gly Ala Pro Gly Ile Ala Gly Ala Pro Gly Phe Pro Gly Ala Arg Gly
                405                 410                 415

Pro Ser Gly Pro Gln Gly Pro Gly Gly Pro Pro Gly Pro Lys Gly Asn
            420                 425                 430

Ser Gly Glu Pro Gly Ala Pro Gly Ser Lys Gly Asp Thr Gly Ala Lys
            435                 440                 445

Gly Glu Pro Gly Pro Val Gly Val Gln Gly Pro Pro Gly Pro Ala Gly
            450                 455                 460

Glu Glu Gly Lys Arg Gly Ala Arg Gly Glu Pro Gly Pro Thr Gly Leu
465                 470                 475                 480

Pro Gly Pro Pro Gly Glu Arg Gly Gly Pro Gly Ser Arg Gly Phe Pro
                485                 490                 495

Gly Ala Asp Gly Val Ala Gly Pro Lys Gly Pro Ala Gly Glu Arg Gly
            500                 505                 510

Ser Pro Gly Pro Ala Gly Pro Lys Gly Ser Pro Gly Glu Ala Gly Arg
        515                 520                 525

Pro Gly Glu Ala Gly Leu Pro Gly Ala Lys Gly Leu Thr Gly Ser Pro
        530                 535                 540

Gly Ser Pro Gly Pro Asp Gly Lys Thr Gly Pro Pro Gly Pro Ala Gly
545                 550                 555                 560

Gln Asp Gly Arg Pro Gly Pro Pro Gly Pro Pro Gly Ala Arg Gly Gln
                565                 570                 575

Ala Gly Val Met Gly Phe Pro Gly Pro Lys Gly Ala Ala Gly Glu Pro
            580                 585                 590

Gly Lys Ala Gly Glu Arg Gly Val Pro Gly Pro Pro Gly Ala Val Gly
        595                 600                 605

Pro Ala Gly Lys Asp Gly Glu Ala Gly Ala Gln Gly Pro Pro Gly Pro
        610                 615                 620

Ala Gly Pro Ala Gly Glu Arg Gly Glu Gln Gly Pro Ala Gly Ser Pro
625                 630                 635                 640

Gly Phe Gln Gly Leu Pro Gly Pro Ala Gly Pro Pro Gly Glu Ala Gly
```

-continued

```
                645                 650                 655
Lys Pro Gly Glu Gln Gly Val Pro Gly Asp Leu Gly Ala Pro Gly Pro
            660                 665                 670
Ser Gly Ala Arg Gly Glu Arg Gly Phe Pro Gly Glu Arg Gly Val Gln
            675                 680                 685
Gly Pro Pro Gly Pro Ala Gly Pro Arg Gly Ala Asn Gly Ala Pro Gly
            690                 695                 700
Asn Asp Gly Ala Lys Gly Asp Ala Gly Ala Pro Gly Ala Pro Gly Ser
705                 710                 715                 720
Gln Gly Ala Pro Gly Leu Gln Gly Met Pro Gly Glu Arg Gly Ala Ala
            725                 730                 735
Gly Leu Pro Gly Pro Lys Gly Asp Arg Gly Asp Ala Gly Pro Lys Gly
            740                 745                 750
Ala Asp Gly Ser Pro Gly Lys Asp Gly Val Arg Gly Leu Thr Gly Pro
            755                 760                 765
Ile Gly Pro Pro Gly Pro Ala Gly Ala Pro Gly Asp Lys Gly Glu Ser
            770                 775                 780
Gly Pro Ser Gly Pro Ala Gly Pro Thr Gly Ala Arg Gly Ala Pro Gly
785                 790                 795                 800
Asp Arg Gly Glu Pro Gly Pro Pro Gly Pro Ala Gly Phe Ala Gly Pro
            805                 810                 815
Pro Gly Ala Asp Gly Gln Pro Gly Ala Lys Gly Glu Pro Gly Asp Ala
            820                 825                 830
Gly Ala Lys Gly Asp Ala Gly Pro Pro Gly Pro Ala Gly Pro Ala Gly
            835                 840                 845
Pro Pro Gly Pro Ile Gly Asn Val Gly Ala Pro Gly Ala Lys Gly Ala
            850                 855                 860
Arg Gly Ser Ala Gly Pro Pro Gly Ala Thr Gly Phe Pro Gly Ala Ala
865                 870                 875                 880
Gly Arg Val Gly Pro Pro Gly Pro Ser Gly Asn Ala Gly Pro Pro Gly
            885                 890                 895
Pro Pro Gly Pro Ala Gly Lys Glu Gly Gly Lys Gly Pro Arg Gly Glu
            900                 905                 910
Thr Gly Pro Ala Gly Arg Pro Gly Glu Val Gly Pro Pro Gly Pro Pro
            915                 920                 925
Gly Pro Ala Gly Glu Lys Gly Ser Pro Gly Ala Asp Gly Pro Ala Gly
            930                 935                 940
Ala Pro Gly Thr Pro Gly Pro Gln Gly Ile Ala Gly Gln Arg Gly Val
945                 950                 955                 960
Val Gly Leu Pro Gly Gln Arg Gly Glu Arg Gly Phe Pro Gly Leu Pro
            965                 970                 975
Gly Pro Ser Gly Glu Pro Gly Lys Gln Gly Pro Ser Gly Ala Ser Gly
            980                 985                 990
Glu Arg Gly Pro Pro Gly Pro Met Gly Pro Pro Gly Leu Ala Gly Pro
            995                1000                1005
Pro Gly Glu Ser Gly Arg Glu Gly Ala Pro Ala Glu Gly Ser Pro
       1010                1015                1020
Gly Arg Asp Gly Ser Pro Gly Ala Lys Gly Asp Arg Gly Glu Thr Gly
1025                1030                1035                1040
Pro Ala Gly Pro Pro Gly Ala Pro Gly Ala Pro Gly Ala Pro Gly Pro
                1045                1050                1055
Val Gly Pro Ala Gly Lys Ser Gly Asp Arg Gly Glu Thr Gly Pro Ala
            1060                1065                1070
```

```
Gly Pro Ala Gly Pro Val Gly Pro Val Gly Ala Arg Gly Pro Ala Gly
        1075                1080                1085
Pro Gln Gly Pro Arg Gly Asp Lys Gly Glu Thr Gly Glu Gln Gly Asp
    1090                1095                1100
Arg Gly Ile Lys Gly His Arg Gly Phe Ser Gly Leu Gln Gly Pro Pro
1105                1110                1115                1120
Gly Pro Pro Gly Ser Pro Gly Glu Gln Gly Pro Ser Gly Ala Ser Gly
            1125                1130                1135
Pro Ala Gly Pro Arg Gly Pro Pro Gly Ser Ala Gly Ala Pro Gly Lys
        1140                1145                1150
Asp Gly Leu Asn Gly Leu Pro Gly Pro Ile Gly Pro Pro Gly Pro Arg
    1155                1160                1165
Gly Arg Thr Gly Asp Ala Gly Pro Val Gly Pro Pro Gly Pro Pro Gly
    1170                1175                1180
Pro Pro Gly Pro Pro Gly Pro Pro Ser Ala Gly Phe Asp Phe Ser Phe
1185                1190                1195                1200
Leu Pro Gln Pro Pro Gln Glu Lys Ala His Asp Gly Gly Arg Tyr Tyr
        1205                1210                1215
Arg Ala Asp Asp Ala Asn Val Val Arg Asp Arg Asp Leu Glu Val Asp
        1220                1225                1230
Thr Thr Leu Lys Ser Leu Ser Gln Gln Ile Glu Asn Ile Arg Ser Pro
    1235                1240                1245
Glu Gly Ser Arg Lys Asn Pro Ala Arg Thr Cys Arg Asp Leu Lys Met
    1250                1255                1260
Cys His Ser Asp Trp Lys Ser Gly Glu Tyr Trp Ile Asp Pro Asn Gln
1265                1270                1275                1280
Gly Cys Asn Leu Asp Ala Ile Lys Val Phe Cys Asn Met Glu Thr Gly
            1285                1290                1295
Glu Thr Cys Val Tyr Pro Thr Gln Pro Ser Val Ala Gln Lys Asn Trp
        1300                1305                1310
Tyr Ile Ser Lys Asn Pro Lys Asp Lys Arg His Val Trp Phe Gly Glu
    1315                1320                1325
Ser Met Thr Asp Gly Phe Gln Phe Glu Tyr Gly Gly Gln Gly Ser Asp
    1330                1335                1340
Pro Ala Asp Val Ala Ile Gln Leu Thr Phe Leu Arg Leu Met Ser Thr
1345                1350                1355                1360
Glu Ala Ser Gln Asn Ile Thr Tyr His Cys Lys Asn Ser Val Ala Tyr
        1365                1370                1375
Met Asp Gln Gln Thr Gly Asn Leu Lys Lys Ala Leu Leu Leu Lys Gly
        1380                1385                1390
Ser Asn Glu Ile Glu Ile Arg Ala Glu Gly Asn Ser Arg Phe Thr Tyr
    1395                1400                1405
Ser Val Thr Val Asp Gly Cys Thr Ser His Thr Gly Ala Trp Gly Lys
    1410                1415                1420
Thr Val Ile Glu Tyr Lys Thr Thr Lys Ser Ser Arg Leu Pro Ile Ile
1425                1430                1435                1440
Asp Val Ala Pro Leu Asp Val Gly Ala Pro Asp Gln Glu Phe Gly Phe
            1445                1450                1455
Asp Val Gly Pro Val Cys Phe Leu
        1460

<210> SEQ ID NO 3
<211> LENGTH: 20
```

```
<212> TYPE: DNA
<213> ORGANISM: Homo sapiens
<220> FEATURE:
<223> OTHER INFORMATION: Antisense oligonucleotide

<400> SEQUENCE: 3
ggacgaccag gttttccagc                                               20

<210> SEQ ID NO 4
<211> LENGTH: 20
<212> TYPE: DNA
<213> ORGANISM: Homo sapiens
<220> FEATURE:
<223> OTHER INFORMATION: Antisense oligonucleotide

<400> SEQUENCE: 4
gcagcaccag cagggccagg                                               20

<210> SEQ ID NO 5
<211> LENGTH: 20
<212> TYPE: DNA
<213> ORGANISM: Homo sapiens
<220> FEATURE:
<223> OTHER INFORMATION: Antisense oligonucleotide

<400> SEQUENCE: 5
gccaggagca ccaggttcac                                               20

<210> SEQ ID NO 6
<211> LENGTH: 20
<212> TYPE: DNA
<213> ORGANISM: Homo sapiens
<220> FEATURE:
<223> OTHER INFORMATION: Antisense oligonucleotide

<400> SEQUENCE: 6
cttcctctcc agcagggcca                                               20

<210> SEQ ID NO 7
<211> LENGTH: 20
<212> TYPE: DNA
<213> ORGANISM: Homo sapiens
<220> FEATURE:
<223> OTHER INFORMATION: Antisense oligonucleotide

<400> SEQUENCE: 7
gccttgccgg gctctccagc                                               20

<210> SEQ ID NO 8
<211> LENGTH: 20
<212> TYPE: DNA
<213> ORGANISM: Homo sapiens
<220> FEATURE:
<223> OTHER INFORMATION: Antisense oligonucleotide

<400> SEQUENCE: 8
cgggaacacc tcgctctcca                                               20

<210> SEQ ID NO 9
<211> LENGTH: 20
<212> TYPE: DNA
<213> ORGANISM: Homo sapiens
<220> FEATURE:
<223> OTHER INFORMATION: Antisense oligonucleotide

<400> SEQUENCE: 9
```

```
gcaggaccga cagcgccagg                                                      20

<210> SEQ ID NO 10
<211> LENGTH: 20
<212> TYPE: DNA
<213> ORGANISM: Homo sapiens
<220> FEATURE:
<223> OTHER INFORMATION: Antisense oligonucleotide

<400> SEQUENCE: 10
tccatctttg ccagcaggac                                                      20

<210> SEQ ID NO 11
<211> LENGTH: 20
<212> TYPE: DNA
<213> ORGANISM: Homo sapiens
<220> FEATURE:
<223> OTHER INFORMATION: Antisense oligonucleotide

<400> SEQUENCE: 11
ggtccctgag ctccagcctc                                                      20

<210> SEQ ID NO 12
<211> LENGTH: 19
<212> TYPE: DNA
<213> ORGANISM: Homo sapiens
<220> FEATURE:
<223> OTHER INFORMATION: Antisense oligonucleotide

<400> SEQUENCE: 12
ttggccgtca gcaccaggg                                                       19

<210> SEQ ID NO 13
<211> LENGTH: 20
<212> TYPE: DNA
<213> ORGANISM: Homo sapiens
<220> FEATURE:
<223> OTHER INFORMATION: Antisense oligonucleotide

<400> SEQUENCE: 13
tttctcgcca gcagggccag                                                      20

<210> SEQ ID NO 14
<211> LENGTH: 20
<212> TYPE: DNA
<213> ORGANISM: Homo sapiens
<220> FEATURE:
<223> OTHER INFORMATION: Antisense oligonucleotide

<400> SEQUENCE: 14
ctcgatctgc tggctcaggc                                                      20
```